(12) United States Patent
Chiorazzi et al.

(10) Patent No.: US 7,316,906 B2
(45) Date of Patent: *Jan. 8, 2008

(54) CD38 AS A PROGNOSTIC INDICATOR IN B CELL CHRONIC LYMPHOCYTIC LEUKEMIA

(75) Inventors: Nicholas Chiorazzi, Tenafly, NJ (US); Rajendra N. Damle, Lynbrook, NY (US); Tarun Wasil, St John's (CA)

(73) Assignee: The Feinstein Institute for Medical Research, Manhasset, NY (US)

( * ) Notice: Subject to any disclaimer, the term of this patent is extended or adjusted under 35 U.S.C. 154(b) by 721 days.

This patent is subject to a terminal disclaimer.

(21) Appl. No.: 10/211,394

(22) Filed: Aug. 2, 2002

(65) Prior Publication Data

US 2003/0082593 A1 May 1, 2003

Related U.S. Application Data

(63) Continuation of application No. 09/415,393, filed on Oct. 8, 1999, now Pat. No. 6,506,551.

(51) Int. Cl.
*G01N 33/53* (2006.01)
*G01N 33/567* (2006.01)
*G01N 33/574* (2006.01)
*C12Q 1/00* (2006.01)

(52) U.S. Cl. .................. 435/7.1; 435/4; 435/7.2; 435/7.21; 435/7.23

(58) Field of Classification Search .......... 435/7.1
See application file for complete search history.

(56) References Cited

U.S. PATENT DOCUMENTS 6,506,551 B1 * 1/2003 Chiorazzi et al. ............. 435/4

OTHER PUBLICATIONS

Damle et al (Blood, 1999, 94:1840-1847).*

* cited by examiner

*Primary Examiner*—Susan Ungar
(74) *Attorney, Agent, or Firm*—Amster, Rothstein & Ebenstein LLP

(57) ABSTRACT

The subject invention discloses a method for determining the prognosis and probable clinical course of a subject diagnosed with B-CLL. Specifically, the invention involves comparing CD38 expression in a biological sample from the subject containing B-CLL cells to a baseline level of CD38 expression, wherein an elevated level of CD38 expression in relation to the baseline level of CD38 expression may indicate poor prognosis or aggressive course of disease in the subject. Also disclosed is a method for determining whether the Ig V genes of the B-CLL cells of a B-CLL patient are mutated, comprising comparing CD38 expression in a biological sample from the subject containing B-CLL cells to a baseline level of CD38 expression, wherein a lower level of CD38 expression in relation to the baseline level indicates IG V gene mutation.

10 Claims, 4 Drawing Sheets

CD38 AS A PROGNOSTIC INDICATOR IN B CELL CHRONIC LYMPHOCYTIC LEUKEMIA

CROSS REFERENCE TO RELATED APPLICATION

This is a continuation of U.S. patent application Ser. No. 09/415,393, filed Oct. 8, 1999, now U.S. Pat. No. 6,506,551 B1.

STATEMENT OF GOVERNMENT INTEREST

This invention is supported in part by US PHS grant AI 10811 from the NIH NIAID. As such, the U.S. Government may have certain rights in this invention.

BACKGROUND OF THE INVENTION

B cell chronic lymphocytic leukemia (B-CLL) is the most common leukemia in the Western world (Rai K, Patel D: *Chronic Lymphocytic Leukemia*, in Hoffman R, Benz E, Shattil S, Furie B, Cohen H, Silberstein L (eds): *Hematology: Basic Principles and Practice* (ed 2nd). New York, Churchill Livingstone, 1995, p 1308). Around 7,500 individuals develop and 5,000 die from this disease each year (Landis S H, et al., *CA Cancer J Clin* 48:6, 1998). Age is an important factor, since the incidence of B-CLL increases linearly with each decade above the age of 40 (Ries L, et al: *SEER cancer statistics review* 1973-1991: Tables and graphs., in Ries L, et al (eds). Bethesda, NIH, 1994; Rai K R, *Clin Geriatr Med* 13:245, 1997). In addition, gender is relevant, since men outnumber women by an approximate 2:1 ratio (Catovsky D, et al., *Br J Haematol* 72:141, 1989) and may have a worse clinical outcome (Id.; Mandelli F, et al., *J Clin Oncol* 5:398, 1987).

Patients with B-CLL follow heterogeneous clinical courses. Some survive for prolonged periods without definitive therapy, while others die rapidly despite aggressive treatment (Rai K, Patel D: *Chronic Lymphocytic Leukemia*, in Hoffman R, et al. (eds): *Hematology: Basic Principles and Practice* (ed 2nd). New York, Churchill Livingstone, 1995, p 1308; Zwiebel J A, Cheson B D, *Semin Oncol* 25:42, 1998). While various staging systems, most notably the Rai and Binet staging systems, have been developed to address this clinical heterogeneity (Rai K R, et al., *Blood* 46, 219, 1975; Binet J L, et al., *Cancer* 48:198, 1981; and Rai K: *A critical analysis of staging in CLL*, in Gail R, Rai K (eds): *Chronic Lymphocytic Leukemia. Recent Progress and Future Directions*. New York, Alan R Liss, 1987, p 253), they cannot accurately predict whether an early or intermediate stage patient will experience an indolent or aggressive course of disease. Specifically, since these systems consider gross manifestations of the disease, including the level of blood and marrow lymphocyte counts, the size and distribution of the lymph nodes, the spleen size, the degree of anemia and the patient's blood platelet count, they can only identify patients with poor prognostic outcome when the disease has progressed to a more advanced state.

At the present time, there is no known treatment for B-CLL which has been shown to definitively increase life expectancy. Consequently, only patients classified in the advanced stages of B-CLL have been considered for aggressive treatment such as chemotherapy, radiation therapy, surgery, immunotherapy or transplantation. These treatments may exact a severe physical and emotional toll on the patient without necessarily improving outcome; in some instances, B-CLL patients may even succumb from the rigors of treatment rather than from the effects of B-CLL. Patients classified in the early stages of B-CLL, who may be in better physical condition to receive more aggressive or experimental treatment, generally receive no treatment as long as the condition remains stable. This is for two reasons. First, currently available therapies do not extend life span. Second, there are currently no reliable indicators of which early stage patients will do well and which will do poorly. Further, the unpredictable course of the disease can make interpreting the results of clinical trials difficult, as some early stage patients will follow an indolent course even without the benefit of treatment.

Such drawbacks have led researchers to develop adjuvant prognostic criteria to be used in conjunction with the Rai and Binet staging systems, including several parameters such as lymphocyte doubling time (Montserrat E, et al., *Br J Haematol* 62:567, 1986), circulating levels of $\beta$2-microglobulin (Di Giovanni S, et al., *Acta Haematol* 81:181, 1989; Keating M J, et al., *Blood* 86:606A, 1995 (Abstract)), circulating levels of soluble CD23 (Sarfati M, et al., *Blood* 88:4259, 1996), serum thymidine kinase levels (Kallander C F, et al., *Cancer* 54:2450, 1984; Hallek M, et al., *Blood* 93:1732, 1999), bone marrow histology (Rozman C, et al., *Blood* 64:642, 1984), and cytogenetic abnormalities (Juliusson G, et al., *N Engl J Med* 323:720, 1990).

An accurate prognostic indicator for B-CLL not related to the symptoms of advanced disease would be desirable in the treatment and case management of B-CLL patients. Specifically, a prognostic indicator that could be evaluated at the cellular level at the earliest stages of the disease (before onset of thrombocytopenia, anemia, spleen and liver enlargement, etc.) would help physicians identify which patients would progress to a more advanced state of the disease and allow the option of more aggressive or experimental treatment at a much earlier stage. Additionally, clinical trials of new drugs or experimental therapies could be directed to patients depending upon their prognostic outlook, thereby allowing for more relevant results in clinical trials. Ideally, the expression of such a prognostic indicator would remain constant over the course of disease.

B-CLL is characterized by the clonal accumulation of $CD5^+$ cells (Caligaris-Cappio, et al., *J Exp Med* 155:623-8, 1982). Although these cells originally were considered antigen inexperienced "virgin" lymphocytes, recent data indicate that at least half of these cases represent expansions of previously-triggered, post germinal center "memory" B cells (Schroeder and Dighiero, *Immunol Today* 15:288-294, 1994; Fais, et al., *J Clin Invest* 102:1515-1525, 1998). This conclusion is based on the presence of significant numbers of somatic mutations in the immunoglobulin (Ig) heavy (H) chain variable region (V) genes. In a study of 83 (64 $IgM^+$ and 19 non-$IgM^+$) B-CLL cases, the inventor and colleagues found significant numbers of $V_H$ mutations in approximately 50% of the $IgM^+$ and 75% of the non-IgM+ (IgG and IgA) cases (Fais, et al, supra, 1998). Taken together with newer studies undertaken by the inventor and colleagues, $V_H$ and $V_L$ sequencing data suggest that approximately 60% of B-CLL cases can be considered to be derived from post-germinal center (GC) memory B-cells. Thus, the inventor hypothesized that B-CLL cases can be divided into two categories, namely cells clonally derived from post-germinal center memory B-cells (hereinafter referred to as "post-GC B cells") and pre-germinal center B cells (hereinafter referred to as "pre-GC B cells"), some of which may be antigen inexperienced "virgin" lymphocytes or activated B cells that were transformed without entering a germinal center, and these categories may be relevant to prognosis.

The expression of specific cell surface markers distinguishes subsets of normal human B cells that differ in differentiation and activation stages and in biologic properties (Clark and Lane, *Ann Rev Immunol* 9:97-127, 1991). In particular, analyses of CD38 and IgD expression have been especially useful in distinguishing B-cells at various stages of differentiation from naive through memory cells (Pascual, et al., *J Exp Med* 180:329-339, 1994; Zupo, et al., *Blood*, 88:1365-1374, 1996).

Accordingly, the inventor sought to determine whether the distinctions based upon surface membrane phenotype of B-CLL cells ($CD38^+$ or $CD38^-$) or Ig V gene mutation status might predict different clinical courses and outcomes for B-CLL patients notwithstanding similar staging of these patients using conventional staging methods. Undertaking the experiments described herein, the inventor has discovered a strong correlation between CD38 expression and Ig V gene mutation, and a strong independent correlation between each of CD38 expression and IgV gene mutation and patient prognosis. Since CD38 expression in a subject's B-CLL cells may be easily and relatively inexpensively determined through various methods known and commonly used in the art, CD38 expression in particular may be a valuable prognostic indicator in B-CLL cases and should aid in the management of B-CLL patients.

SUMMARY OF THE INVENTION

The present invention discloses a method for determining the prognosis of a subject with chronic lymphocytic leukemia ("B-CLL"), comprising determining whether the subject's B-CLL cells have been clonally expanded from post-GC B cells (post-germinal center memory B-cells) or pre-GC B cells (pre-germinal center B cells, some of which may be antigen inexperienced "virgin" lymphocytes or activated B cells that were transformed without entering a germinal center), wherein clonal expansion from post-GC B cells may be indicative of an indolent course of B-CLL in the subject or favorable prognosis, and clonal expansion from pre-GC B cells may be indicative of poor prognosis or an aggressive course of disease.

In one method of the present invention, CD38 expression of B-CLL cells in a biological sample from the subject is compared to a baseline level of CD38 expression of B-CLL cells, wherein an elevated level of CD38 expression in relation to the baseline level of CD38 expression may indicate poor prognosis or aggressive course of disease in the subject. In one embodiment, the percentage of total B-CLL cells which are $CD38^+$ in the biological sample is compared to a baseline percentage of $CD38^+$ B-CLL cells, wherein an elevated percentage of $CD38^+$ B-CLL cells in relation to the baseline percentage of $CD38^+$ B-CLL cells is indicative of poor prognosis. In another embodiment of the invention, the density of CD38 surface membrane expression on the B-CLL cells in a biological sample from the subject is compared to a baseline density of CD38 surface membrane expression of B-CLL cells, wherein an elevated density of CD38 surface membrane expression in relation to the baseline density of CD38 surface membrane expression may indicate poor prognosis.

Also disclosed is a method for determining whether the Ig V genes of the B-CLL cells of a B-CLL patient are mutated, comprising comparing CD38 expression of B-CLL cells (either as a function of relative percentage of $CD38^+$ B-CLL cells, or as a function of the relative density of CD38 surface membrane expression on the B-CLL cells) in a biological sample from the subject to a baseline level of CD38 expression, wherein a lower level of CD38 expression in relation to the baseline level of CD38 expression indicates IG V gene mutation.

Figure 1:
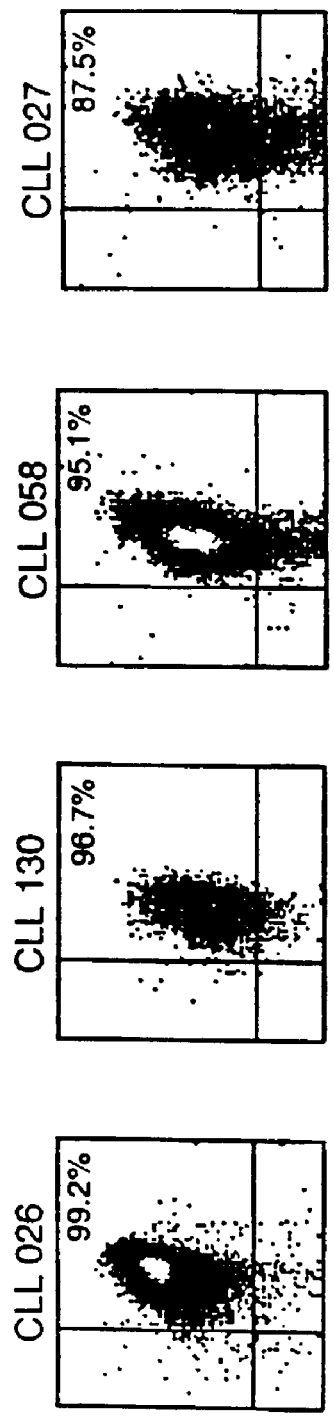
FIG. 1 depicts representative flow cytometric profiles of CD38 expression on mutated and unmutated $CD5^+/CD19^+$ B-CLL cases. B-CLL cases were analyzed by flow cytometry after exposure to anti-CD19-APC, anti-CD5-FITC, and anti-CD38-PE monoclonal antibodies. The events illustrated were obtained by gating on cells expressing CD19. Density plots of CD38 and CD5 expression are shown for eight representative B-CLL cases. The upper four cases had no mutations in either the $V_H$ or $V_L$ genes, whereas the lower four cases had mutations in the $V_H$ and/or $V_L$ genes.
Figure 1:
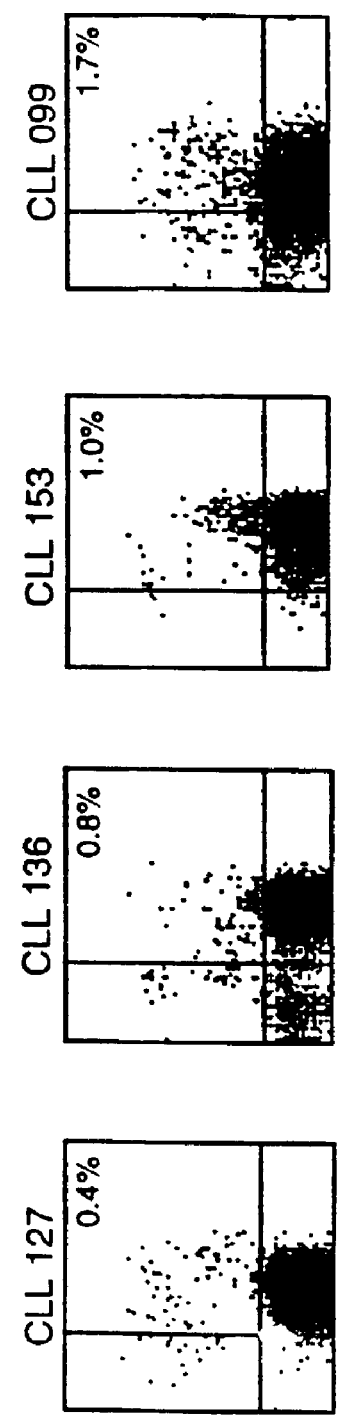

The median survival of the mutated group is 17 years; the median survival of the unmutated group is 9 years (p=0.0007; log-rank test). Panel B is a Kaplan-Meier plot comparing numbers of $CD38^+$ B-CLL cells with survival among the cases within the Rai intermediate risk category ($\geq 30\%$: 11 cases; <30%: 9 cases). The median survival of the 30% $CD38^+$ group is 10 years; the median survival of the <30% $CD38^+$ group was not reached in 19 years (p=0.0030; log-rank test). None of the patients in the <30% $CD38^+$ group died during the follow-up period.

DETAILED DESCRIPTION OF THE INVENTION

The present invention provides a method for determining the prognosis or projected clinical course in a subject with B cell chronic lymphocytic leukemia ("B-CLL"). In particular, the method of the present invention discloses an immunophenotypic prognostic indicator which predicts whether the course of disease in a specific B-CLL patient will be aggressive or indolent, thereby aiding the clinician in managing the patient and evaluating the modality of treatment to be used.

Since at the current time there are no known treatments that will definitively increase the life expectancy of persons diagnosed with B-CLL, clinicians must balance the rigors of aggressive or experimental treatment with the likelihood that such treatment will result in tangible benefit to the patient. In fact, some B-CLL patients succumb to the combined effects of treatment and B-CLL rather than to the effects of B-CLL alone. Accordingly, more aggressive treatment, such as radiation therapy, chemotherapy, transplants and immunotherapy, has traditionally been reserved for those B-CLL patients already in the advanced stages of B-CLL who stage higher in the conventional Rai and Binet staging systems. However, these patients may be the most ill equipped to handle the rigors of such treatment.

Additionally, the heterogeneous course of B-CLL complicates the evaluation of clinical trials, as it is difficult to distinguish patients who are effectively responding to the therapy being administered from patients who would have never progressed to a more advanced stage of the disease regardless of treatment. Accordingly, an immunophenotypic prognostic indicator which is predictive of a patient's clinical course, notwithstanding the conventional stage of the disease, will aid clinicians in better evaluating treatment options, as well as greatly enhancing the value of clinical studies by better distinguishing the effects of treatment.

The present invention generally disclose a method for determining the prognosis of a subject with chronic lymphocytic leukemia ("B-CLL"), comprising determining whether the subject's B-CLL cells (B-CLL B cells) have been clonally expanded from post-GC B cells (post-germinal center memory B-cells) or pre-BC B cells (pre-germinal center B cells, some of which may be antigen inexperienced "virgin" lymphocytes or activated B cells that were transformed without entering a germinal center). Clonal expansion from post-GC B cells may be indicative of an indolent course of B-CLL in the subject or favorable prognosis, while clonal expansion from pre-GC B cells may be indicative of poor prognosis or an aggressive course of disease.

Specifically, in the preferred embodiment of the present invention, CD38 expression of B-CLL cells in a biological sample from the subject is compared to a baseline level of CD38 expression of B-CLL cells, wherein an elevated level of CD38 expression in relation to the baseline level of CD38 expression may indicate poor prognosis or aggressive course of disease in the subject. The method may be performed using any tissue containing B-CLL cells, including but not limited to spleen, lymph nodes, bone marrow, lymph, a whole blood sample from the subject or a whole blood sample that has been treated and processed to isolate the peripheral blood mononuclear cells ("PBMC").

In one embodiment, the percentage of total B-CLL cells in the biological sample which are CD38$^+$ is compared to a baseline percentage of CD38$^+$ B-CLL cells, wherein an elevated percentage of CD38$^+$ B-CLL cells in relation to the baseline percentage of CD38$^+$ B-CLL cells is indicative of poor prognosis, and a lower percentage of CD38$^+$ B-CLL cells in relation to the baseline percentage is indicative of a favorable prognosis or indolent course of disease. Alternatively, the density of CD38 surface membrane expression on the B-CLL cells in a biological sample from the subject is compared to a baseline density of CD38 surface membrane expression on B-CLL cells, wherein an elevated density of CD38 surface membrane expression in relation to the baseline density surface membrane expression may indicate poor prognosis, and a lower density of CD38 surface membrane expression in relation to the baseline density of CD38 surface membrane expression may indicate a favorable prognosis or a more indolent course of disease.

In both embodiments, i.e., comparing the relative percentage of CD38$^+$ B-CLL cells (as a percentage of the B-CLL population in total, such as a percentage of CD5$^+$/CD19$^+$ lymphocytes) or comparing the relative density of CD38 surface membrane expression on B-CLL cells in the biological sample, the level of CD38 expression may be determined by any method currently known in the art, including any applicable direct or indirect immunofluorescence technique. Further, where relative density of CD38 surface membrane expression on the B-CLL cells in the biological sample is being determined, mean channel fluorescence may be used. In a preferred embodiment of the invention, the level of CD38$^+$ B-CLL expression is determined using flow cytometry where the cells have been labeled with monoclonal antibodies conjugated with fluorescent dyes or enzymes, although visual immunofluorescence or other methods may also be used. In a specific embodiment, PBMCs are analyzed for surface expression of CD19/CD5/CD38 by triple color immunofluorescence using anti-CD19-APC, anti-CD5-FITC (CD5 being specific to B-CLL cells and CD19 being specific to B lymphocytes, although other combinations of antigens/labeled antibodies or enzymes may be used that are specific to narrow the analyzed pool to B-CLL cells) and anti-CD38-PE antibody conjugates. The preferred antibody conjugate is anti-CD38-PE (Simultest LeucoGATE, from Becton Dickinson Immunocytometry Systems, San Jose, Calif.).

Additionally, it is well within the skill of one of ordinary skill in the art to devise either direct or indirect immunoassay kits (i.e., ELISA or other kits) which use similar antigen/labeled antibody or enzyme combinations to detect levels of CD38 expression. The relative percentage of CD38$^+$ B-CLL cells in relation to a percentage baseline of CD38$^+$ B-CLL cells, or the relative density of CD38 surface membrane expression on B-CLL cells in relation to a baseline density of CD38 surface membrane expression, may be determined by comparing the resulting color, fluorescence or equivalent reaction with a control sample having a predetermined percentage of CD38$^+$ B-CLL cells or density of CD38 (or the relevant epitope of CD38), as appropriate.

While the exact relative percentage of CD38$^+$ B-CLL cells or density of CD38 surface membrane expression that defines poor or favorable prognosis, i.e., the baseline level of CD38 expression of the B-CLL cells, is somewhat arbitrary (as the numerical cut off value may be shifted upward or downward with an attendant loss of accuracy in the prognostic utility of the test), in a preferred embodiment of the invention using the disclosed antibody or one of equivalent avidity and specificity, as well as the disclosed anti-CD38-PE fluorochrome, the relative percentage of CD38$^+$ B-CLL cells indicating poor prognosis is greater than 15%, more preferably is greater than 20%, even more preferably is greater than 25% and most preferably is greater than 30% of the total B-CLL cells in the biological sample. The preferred range may be affected by the specific anti-CD38 monoclonal antibody (mAB) used, as different mABs will have different binding affinities (avidity) for CD38 and may bind to different epitopes of CD38, as well as by the specific fluorochrome used. Further, similar variable parameters exist in isolating the B-CLL population in the biological sample.

That is, the exact preferred baseline may vary depending upon the specific anti-CD5 and anti-CD19 mABs used, and the anti-CD5 and anti-CD19 fluorochrome conjugates used, for the reasons noted above regarding variations in avidity and specificity, as well as the efficiency of the mAB conjugated fluorochrome. Using the mABs and fluorochromes disclosed in the Experimental Details below will yield the preferred baseline range of CD38 expression as disclosed herein. However, all other elements being the same, mABs with a lower avidity will have a correspondingly increased baseline range, so that higher densities of CD38 surface membrane expression, or increased relative percentages of CD38$^+$ B-CLL cells, will be required to establish a poor prognosis or aggressive course of disease.

However, it is well within the skill of one of ordinary skill in the art to determine the appropriate CD38 baseline level, by either using the experimental method disclosed herein (that is, comparing levels of CD38 expression among a characterized group of B-CLL patients with a known clinical course), or by comparing the relative avidity and specificity of the mABs disclosed herein and the mABs used in any particular instance, as well as the relative efficiency of the particular fluorochrome used, and thereafter deducing the appropriate baseline.

Also disclosed by the present invention is a method for determining whether the Ig V genes of the B-CLL cells of a B-CLL patient are mutated, comprising comparing CD38 expression of B-CLL cells in a biological sample from the subject to a baseline level of CD38 expression of B-CLL cells, wherein a lower level of CD38 expression in relation to the baseline level of CD38 expression indicates IG V gene mutation. In one embodiment of the invention, CD38 expression of B-CLL cells in the biological sample is compared to the baseline level of CD38 expression by comparing the percentage of total B-CLL cells which are CD38$^+$ to a baseline percentage of CD38$^+$ B-CLL cells, wherein a lower percentage of CD38$^+$ B-CLL cells in relation to the baseline percentage is indicative of mutated IgV genes of the B-CLL cells. Preferably, the percentage of CD38$^+$ B-CLL cells indicating Ig V gene mutation is 15% or less, more preferably is 20% or less, even more preferably is 25% or less, and most preferably is 30% or less. In another embodiment of the invention, CD38 expression of the B-CLL cells in the biological sample is compared to the baseline level of CD38 expression by comparing the density of CD38 surface membrane expression of the B-CLL cells in relation to a baseline of CD38 surface membrane expression, wherein a lower density of CD38 surface membrane expression in relation to the baseline is indicative of mutated IgV genes of the B-CLL cells.

The present invention is described in the following Experimental Details Section which is set forth to aid in the understanding of the invention, and should not be construed to limit in any way the invention as defined in the claims which follow thereafter.

Experimental Details Section

Methods (i) Patients

The Institutional Review Boards of North Shore University Hospital, Manhasset, N.Y., and Long Island Jewish Medical Center, New Hyde Park, N.Y., approved these studies. The patients in this study are a subset (n=47) of the well-defined cohort (n=64) of randomly chosen, typical IgM$^+$ B-CLL patients described previously (Fais F, et al., *J Clin Invest* 102:1515, 1998). Patients were selected for the present study based on the availability of detailed clinical histories (Don Monti Division of Medical Oncology, North Shore University Hospital, and the Hematology/Oncology Division, Long Island Jewish Medical Center) and the availability of DNA sequences for both the Ig V$_H$ (Fais F, et al., supra, *J Clin Invest* 102:1515, 1998) and V$_L$ (Ghiotto et al., in preparation) genes in each case. The clinical courses of the patients that were analyzed in this study were not significantly different from those that could not be studied because of lack of sample or follow-up. There were 34 males and 13 females in this group, with a mean age of 63.4 years (range: 38-80). The mean ages of the unmutated (mean: 61.3; range 38-79) and mutated (mean: 65.5; range: 47-80) cases or of the $\geq$30% CD38$^+$ (mean: 63.5; range 38-79) and <30% CD38$^+$ (mean: 63.6; range 44-79) cases were similar. Fresh or cryopreserved B-CLL cells were available for surface marker analyses on 37 patients (20 unmutated and 17 mutated). These samples had been obtained at various points in the clinical follow-up of these patients. There were no differences in the timing of sample acquisition between the unmutated and mutated groups.

(ii) Cellular Immunophenotypic Analysis

The following antibody conjugates were used: anti-CD23-fluorescein isothiocyanate (FITC; Immunotech, Inc., Westbrook, Me.), goat anti-human IgD-FITC (Southern Biotechnology Associates, Birmingham, Ala.), and anti-CD5-FITC, anti-CD5-phycoerythrin (PE), anti-CD38-PE, anti-CD19-allophycocyanin, anti-CD45-FITC and anti-CD14-PE (Simultest LeucoGATE; all from Becton Dickinson Immunocytometry Systems, San Jose, Calif.).

Peripheral blood mononuclear cells (PBMC) were separated from heparinized venous blood by density gradient centrifugation using Ficoll-Paque (Pharmacia LKB Biotechnology, Piscataway, N.J.), and used either immediately or after thawing samples that had been cryopreserved with a programmable cell freezing machine (CryoMed, Mt. Clemens, Mich.). PBMCs were analyzed for surface expression of CD19/CD5/CD38 and CD19/IgD/CD38 and CD19/CD5/CD23 by triple color immunofluorescence (Fais F, et al., *J Clin Invest* 98:1659, 1996). For the detection of CD19/CD5/CD38-expressing cells, mAb labeled with the following fluorochrome were used: anti-CD19-APC, anti-CD5-FITC, and anti-CD38-PE; for the detection of CD19/IgD/CD38-expressing cells, anti-CD19-APC, anti-IgD-FITC, and anti-CD38-PE mAb were used; for the detection of CD19/CD5/CD23-expressing cells, anti-CD19-APC, anti-CD23-FITC, and anti-CD5-PE mAb were used. Isotype-matched negative controls were used in all assays to determine positive from negative results. Flow cytometric analyses were performed on a Becton-Dickinson FACS Calibur flow cytometer equipped with argon and red diode lasers. Measurements of forward and side scatter were combined with CD45 and CD14 determinations to identify lymphocytes and exclude monocytes. The CellQuest software system was used to acquire and analyze data.

(iii) Preparation of RNA and cDNA Synthesis

Total RNA was isolated from either fresh or cryopreserved B-CLL cells using Ultraspec RNA (Biotecx Laboratories, Houston, Tex.) according to the manufacturer's instructions. Two μg of RNA were reverse transcribed to cDNA using M-MLV reverse transcriptase (GIBCO BRL, Life Technologies, Grand Island, N.Y.) and 20 pmol of oligo dT primer in a total volume of 20 μl (Fais, et al., *J. Clin. Invest.*, 102(8), 1998, 1515-1525). These reactions were carried out at 42° C. for 1 hr, heated at 65° C. for 10 minutes, and then diluted to a final volume of 100 μl.

To determine the sequence of the B-CLL cells, 3 μl of cDNA were amplified using a sense $V_H$ leader family specific primer in conjunction with an antisense 19mer $C_H$ primer. The reaction was carried out in 50 μl using 20 pm of each primer and cycled with a Perkin Elmer Cetus 9600 apparatus (Emeryville, Calif.) as follows: denaturation at 94° C. for 30 sec.; annealing at 55° C. for 30 sec.; and extension at 72° C. for 1 min. After 35 cycles, extension was continued at 72° C. for an additional 10 min.

The $V_H$ PCR product was either sequenced in both directions by the dideoxy-chain termination method using fluorescent-labeled ddNTP and TAQ polymerase (Applied Biosystems, I System, Foster City, Calif.) and an automated sequencer (Applied Biosystems, Foster City, Calif.). Sequencing was performed either directly after purification of PCR products with Wizard PCR Preps (Promega, Madison, Wis.), or after cloning into TA vector (Invitrogen, San Diego, Calif.). When the cloning approach was used, multiple colonies were chosen randomly and sequenced.

The B-CLL sequences obtained were compared with those in the V BASE directory using MacVector software, version 6.0 (Eastman Kodak Co., New Haven, Conn.) to determine the most similar germline VH gene and the degree of difference from this germline gene. Similar methods were used to obtain the $V_L$ gene sequences and determine the degree of difference from the germ line gene. However, $V_L$ genes were amplified using a sense $V_L$ leader family specific primer in conjunction with an antisense $C_L$ primer.

(iv) Statistical Analyses

The percentages of $CD5^+/CD19^+$ B cells that co-expressed CD38 or IgD or CD23 were determined for each patient and statistical differences between the unmutated and mutated groups analyzed using the Mann-Whitney test. Patients were also classified according to the percentage of B-CLL cells expressing CD38 into $\geq 30\%$ $CD38^+$ and $<30\%$ $CD38^+$ groups.

To determine the degree of association between the individual patients based on the actual percentages of CD38-expressing cells and on the V gene mutation status or on the percentages of CD23-expressing cells, the Spearman coefficient was calculated. To determine the degree of association between the patients classified into two groups based on percentages of CD38-expressing cells and on the V gene mutation status, the Kappa coefficient was used. Standard methods for estimating proportions and associated exact confidence intervals (CI) were used for estimating sensitivity of high numbers of $CD38^+$ B-CLL cells ($\geq 30\%$) as a marker for "unmutated" V genes. In standard epidemiological terminology, the unmutated gene corresponded to the "disease" state and accordingly sensitivity was computed using the number of patients with unmutated genes as the denominator. Similarly, specificity of low numbers of $CD38^+$ B-CLL cells ($<30\%$) was computed using the patients with mutated genes as the denominator. Accuracy was defined as the percentage of patients who were classified correctly as unmutated or mutated using the CD38 criteria. Positive and negative predictive values were computed using Bayes' Rule.

Comparisons of V gene mutation status and CD38 expression with clinical course were made "blindly". The investigator who reviewed the clinical histories of these patients was unaware of the laboratory data during the retrospective chart review. The two-tailed Fisher's Exact test was used to determine whether chemotherapy requirements, Rai stage at diagnosis, or gender were significantly associated with V gene mutation status or with CD38 percentage. Survival analyses were performed using the Kaplan-Meier product-limit method and the log-rank test.

Results (i) Percentages of $CD38^+$ B-CLL Cells Among the Unmutated and Mutated Cases The DNA sequences of the Ig $V_H$ (Fais F, et al, supra, *J Clin Invest* 102:1515, 1998) and $V_L$ (Ghiotto et al., in preparation) genes expressed by the leukemic cells of the 47 typical $IgM^+$ B-CLL cases included in this study were determined previously. Based on the numbers of somatic mutations detected in these genes, the cases were divided into two categories: "unmutated" or "mutated". As per current convention, "unmutated" cases were defined as those with <2% differences from the most similar germline gene in both the expressed $V_H$ and $V_L$ genes; "mutated" cases were defined as those in which the B-CLL cells displayed $\geq 2\%$ differences in either the expressed $V_H$ or $V_L$ gene.

To determine whether these genetic differences reflected cellular phenotypic differences, the expression of CD38 and IgD on the B-CLL cells of the 37 patients in whom PBMC were available (20 unmutated and 17 mutated) were analyzed. Analyses of CD38 and IgD expression were chosen for these studies because they distinguish B cells at various stages of differentiation (Clark E A, and Lane P J, *Annu Rev Immunol* 9:97, 1991; Pascual V, et al, *J Exp Med* 180:329, 1994).

The unmutated and mutated B-CLL cases were similar in $CD19^+$ B cells co-expressing CD5, CD23 and IgD, both in the percentages of positive cells and in mean fluorescence intensity (data not shown). However, the percentage of $CD38^+$ cells was dramatically different between the unmutated and mutated cases. FIG. 1 illustrates eight representative B-CLL cases analyzed for CD19/CD5/CD38-expressing cells. The $V_H$ and $V_L$ genes of the four cases listed in the upper panel were not mutated, whereas the $V_H$ and/or $V_L$ genes in the lower panel were mutated. Note that the unmutated cases have a much higher percentage of $CD38^+$ cells among the $CD5^+/CD19^+$ cells than the mutated cases in the lower panel.

When the percentages of $CD38^+$ B-CLL cells in the unmutated and mutated groups were compared statistically, very significant differences were found (means: 63.9% vs. 7.3%, respectively; p=0.00001). The Spearman correlation between the individual percentages of $CD38^+$ B-CLL cells in each case vs the actual percentages of V gene mutations was r=−0.75 (p<0.001), indicating a relatively strong inverse relationship. Accordingly, while CD38 is clearly an independent marker for predicting clinical outlook, the statistically significant inverse relationship between CD38 expression and V gene mutation indicates that measurements of CD38 expression can be used to evaluate the level of V gene mutation. A low to moderate direct correlation existed between the percentages of $CD23^+$ B-CLL cells and the percentage of V gene mutation r=0.42; p=0.01). There was no correlation between CD38 expression and CD23 expression (data not shown).

When the results on percentages of CD38 expressing cells were plotted individually (FIG. 2), the cases could be segregated into two distinct sets, one with $\geq 30\%$ $CD38^+$ cells and the other with $<30\%$ $CD38^+$ cells. The 30% cut off value was chosen empirically based on the observed distributions on the plot, and it is understood that higher or lower cut off value may be chosen though such a cut off point may result in lower accuracy in determining prognosis. Furthermore, an inverse relationship existed between CD38 expression and V gene mutation status. The set with the higher percentages of $CD38^+$ B-CLL cells was comprised solely of unmutated cases, whereas the set with the lower percentages of $CD38^+$ cells contained all of the mutated cases and three of the unmutated cases. The Kappa coefficient calculated for association between these two sets of $CD38^+$ B-CLL cases vs. the unmutated and mutated groups was −0.84, indicating a strong inverse relationship.

Furthermore, high percentages of $CD38^+$ B cells ($\geq 30\%$) indicated the presence of <2% mutations with 100% specificity (95% C.I.: 84-100%). Since three patients with unmutated V genes were found to have <30% $CD38^+$ B-CLL cells (FIG. 2), the sensitivity of using $\geq 30\%$ $CD38^+$ B-CLL cells as a marker for significant percentages of $V_H$ or $V_L$ gene mutations was 85% (95% C.I.: 62-97%). Based on this specificity and sensitivity and on a prevalence of 60% for $\geq 2\%$ mutations in either $V_H$ or $V_L$, the positive predictive value of $\geq 30\%$ $CD38^+$ B cells indicating the "unmutated" genotype was 100%. Conversely, the predictive value of <30% $CD38^+$ B cells indicating the "mutated" genotype was 82%. These CD38 criteria indicate V gene mutation status with 92% accuracy.

The differences in CD38 expression were stable over time and were not influenced by chemotherapy. Sixteen patients (7 with CD38 values $\geq 30\%$ and 9 with <30%) were studied at two or more time points, separated by as much as 6 years. Indeed, the percentages of $CD38^+$ B-CLL cells detected never differed by more than 10% in any instance. One patient with 95% circulating $CD38^+$ B-CLL cells was studied on five occasions over a 24 month period and the percentages of $CD38^+$ cells detected in each sample were very similar (<5% difference).

(ii) Clinical Course and Outcome of the Unmutated vs. Mutated B-CLL Cases

The treatment histories of the patients with unmutated and mutated Ig V region genes were very different (Tbl. 1). Eighteen of the 23 mutated cases (78.3%) required either no chemotherapy (52.2%) or minimal treatment (26.1%), while only 20.8% of the unmutated cases required no (16.6%) or minimal therapy (4.2%). These differences were highly significant (p=0.0001). Furthermore, 79.2% (19/24) of the unmutated cases required continuous chemotherapy or chemotherapy utilizing two or more agents or regimens. Although 18 of these 19 patients (94.7%) received fludarabine, only two achieved a durable clinical response.

TABLE 1

Comparison of Treatment Histories Based on Either Ig V Gene Mutation Status or the Percentages of $CD38^+$ B-CLL Cells

| Treatment | Unmutated | Mutated |
|---|---|---|
| Patients requiring no or minimal treatment* | 20.8% (5/24) | 78.3% (18/23) |
| Patients requiring continuous chemotherapy or chemotherapy with 2 or more agents or regimens | 79.2% (19/24) | 21.7% (5/23) |
| | p = 0.0001† | |

| Treatment | $\geq 30\%$ CD38+ B-CLL Cells | <30% CD38+ B-CLL Cells |
|---|---|---|
| Patients requiring no or minimal treatment* | 23.5% (4/17) | 73.7% (14/19) |
| Patients requiring continuous chemotherapy or chemotherapy with 2 or more agents or regimens | 76.5% (13/17) | 26.3% (5/19) |
| | p = 0.0067† | |

*Minimal treatment is defined as less than 6 months of therapy in the years of follow up.
†Statistical analyses performed using the two-tailed Fisher's exact test.

These significant differences in chemotherapy requirements were reflected in significant differences in survival (FIG. 3A). The median survival of the patients in the unmutated group was 9 years, whereas median survival for the mutated group was not reached for the duration of follow-up (p=0.0001).

Finally, V gene mutation status was compared with the clinical stage at the time of diagnosis using the modified Rai system. The patients stratified to all Rai modified clinical stages at the time of diagnosis (Tbl. 2). Patients who stratify to the Rai intermediate risk group are the most heterogeneous in treatment requirements and survival and represent those in whom outcome is the most difficult to predict (Rai K, et al., supra, in *Hematology: Basic Principles and Practice* (ed $2^{nd}$), p 1308; Zwiebel and Cheson, *Semin Oncol*, 25:42-59, 1998). Therefore, the survival of 25 patients in this group were analyzed (9 mutated cases vs. 16 unmutated cases; FIG. 4A). The median survival of the unmutated cases was 9 years, compared to 17 years for the mutated cases (p=0.0007).

TABLE 2

Comparison of Modified Rai Stage at Diagnosis with Ig V Gene Mutation Status and the Percentages of $CD38^+$ B-CLL Cells

| Stage | Unmutated | Mutated |
|---|---|---|
| Low* | 22.7% (5/22) | 52.4% (11/21) |
| Intermediate | 72.7% (16/22) | 42.9% (9/21) |
| High | 4.6% (1/22) | 4.7% (1/21) |
| | p = 0.123 | |

| | $\geq 30\%$ CD38+ B-CLL Cells | <30% CD38+ B-CLL Cells |
|---|---|---|
| Low † | 20.0% (3/15) | 50.0% (9/18) |
| Intermediate † | 73.3% (11/15) | 50.0% (9/18) |
| High | 6.7% (1/15) | 0.0% (0/18) |
| | p = 0.138 | |

*Comparison of V gene mutation status among patients in the low and intermediate risk categories (p = 0.058; two-tailed Fisher's Exact test).
† Comparison of CD38 expression among patients in the low and intermediate risk categories (p = 0.147; two-tailed Fisher's Exact test).

(iii) Clinical Course and Outcome of B-CLL Cases with $\geq 30\%$ or <30% $CD38^+$ Cells.

Since there was a significant correlation between V gene mutation and CD38 expression by the B-CLL cells, chemotherapy requirements and survival as a function of the percentages of $CD38^+$ leukemic cells were compared. Significant differences were found for both. Seventy three percent (14/19) of the <30% $CD38^+$ cases required either no or minimal chemotherapy, compared with 23.5% (4/17) of the $\geq 30\%$ $CD38^+$ cases (p=0.0067; Tbl. 1). Conversely, 76.5% of the $\geq 30\%$ $CD38^+$ cases required either continuous chemotherapy or chemotherapy with two or more agents or regimens.

Median survival for the patients in the $\geq 30\%$ $CD38^+$ group was 10 years (FIG. 3B). In contrast, this value could not be determined for the patients in the <30% $CD38^+$ group since all patients in this group were alive for the duration of follow-up (p=0.0001). Highly significant differences in survival also were found among the patients in the Rai intermediate risk group (FIG. 4B). Median survival for the ≧30% CD38+ patients was reached in 10 years, whereas all patients in the <30% CD38+ group remained alive throughout the years of follow-up (p=0.003).

(iv) Studies of IgG+ and IgA+ B-CLL Cases.

The preceding observations were also true for a cohort of non-IgM producing (IgG or IgA) B-CLL patients (n=16), whose V gene sequence analyses were published previously (Fais, et al., supra, *J Clin Invest* 102:1515-25, 1998; Hashimoto, et al., supra, *J Exp Med* 181:1507-17, 1995). The median survival of the unmutated non-IgM cases was only 3 years, whereas it was not reached for the mutated cases at 15 years (p=0.004, log-rank test; data not shown). Similar data were obtained when the cases were compared based on CD38 expression, although the small numbers of available samples (n=8) precluded accurate statistical analysis. When these non-IgM+ cases were pooled with the IgM+ cases described above (bringing the total number of patients studied to 63), the median survival for the unmutated group (n=29) was 8 years and for the mutated group (n=34) was not reached for the duration of follow-up (p=0.0001). Similar data were obtained for the CD38 groups: median survival for the ≧30% CD38+ (n=19) was 9 years, whereas median survival for the <30% CD38+ group (n=25) was not reached (p=0.0001).

(v) Gender of the B-CLL Cases Based on Either V Gene Mutation or CD38 Expression The cohort of IgM+ B-CLL patients in this study consisted of 34 males and 13 females (M:F=2.6:1). However, the M:F ratio of the patients stratified by either V gene mutation status or CD38 expression was very different (Tbl. 3).

In the mutated group, males and females were virtually equally distributed, whereas in the unmutated group a marked male predominance was found (M:F ratio=11:1; p=0.003). A similar disparity in gender distribution was seen when the patients were compared based on the percentages of CD38+ B-CLL cells. The numbers of males and females among the <30% CD38+ group were almost equal (M:F=1.1:1), whereas males outnumbered females in the ≧30% CD38+ group (M:F=7.5:1; p=0.031).

TABLE 3

Gender Differences Based on either Ig V Gene Mutation Status or the Percentages of CD38+ B-CLL Cells

|  | Unmutated | Mutated |
|---|---|---|
| Male* | 91.7% (22/24) | 52.2% (12/23) |
| Female* | 8.3% (2/24) | 47.8% (11/23) |
| Male:Female Ratio | 11.0:1 | 1.1:1 |
|  |  | p = 0.003* |

|  | ≧30% CD38+ B-CLL Cells | <30% CD38+ B-CLL Cells |
|---|---|---|
| Male* | 88.2% (15/17) | 52.6% (10/19) |
| Female* | 11.8% (2/17) | 47.4% (9/19) |
| Male:Female Ratio | 7.5:1 | 1.1:1 |
|  |  | p = 0.031* |

*Statistically significant difference in gender distribution between the unmutated and mutated groups and between the ≧30% CD38+ and <30% CD38+ groups (two-tailed Fisher's Exact test).

TABLE 4

Characteristics of the Two Groups of B-CLL Patients

|  | V Gene Status | % of CD38+ B-CLL Cells | Chemotherapy Requirement | Survival | M:F Ratio |
|---|---|---|---|---|---|
| Group 1 | Unmutated | High | Extensive | Shorter | High |
| Group 2 | Mutated | Low | Minimal | Longer | ~Equal |

Discussion

Figure 3:
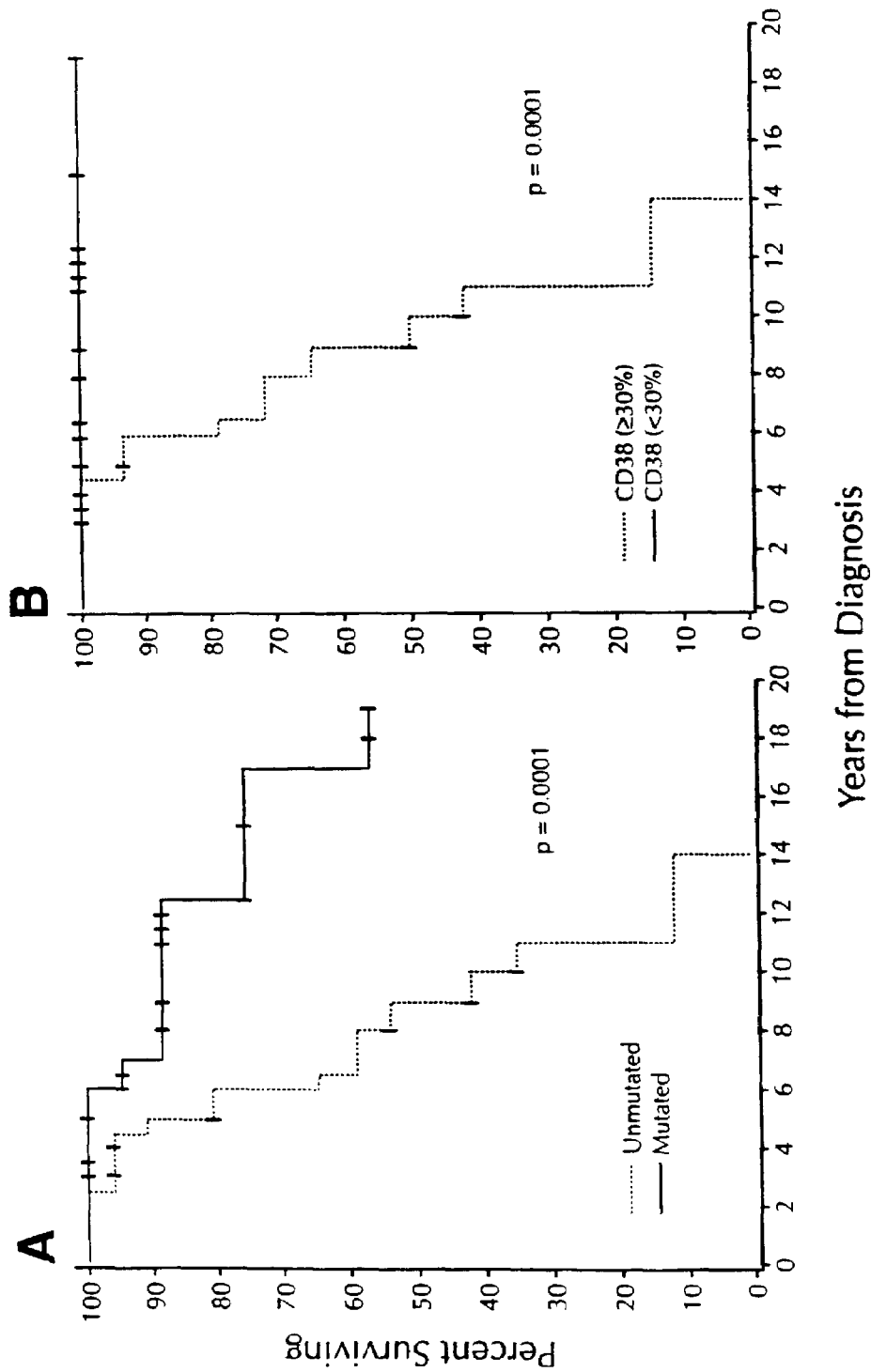
FIG. 3 depicts survival based on V gene mutation status and CD38 expression. Panel A is a Kaplan-Meier plot comparing survival based on the absence ("unmutated": ....) or presence ("mutated": —) of significant numbers ($\geq 2\%$) of V gene mutations in 47 B-CLL cases (unmutated: 24 cases; mutated: 23). The median survival of the unmutated group is 9 years; the median survival of the mutated group was not reached in 19 years; p=0.0001; log-rank test). Panel B is a Kaplan-Meier plot comparing survival based on the detection of $\geq 30\%$ ( . . . ) or <30% $CD38^+$ B-CLL cells ($\geq 30\%$: 17 cases; <30%: 19). The median survival of the $\geq 30\%$ $CD38^+$ group is 10 years; the median survival of the <30% $CD38^+$ group was not reached in 19 years (p=0.0001; log-rank test).

The preceding data indicate that Ig V gene mutation status and CD38 expression are both distinct and important prognostic indicators of clinical course and outcome in B-CLL. Indeed, those patients in either the unmutated or ≧30% CD38+ groups experienced a worse clinical course than those patients in the mutated or <30% CD38+ groups. This was true for both chemotherapy requirements (Tbl. 1) and survival (FIG. 3).

Figure 4:
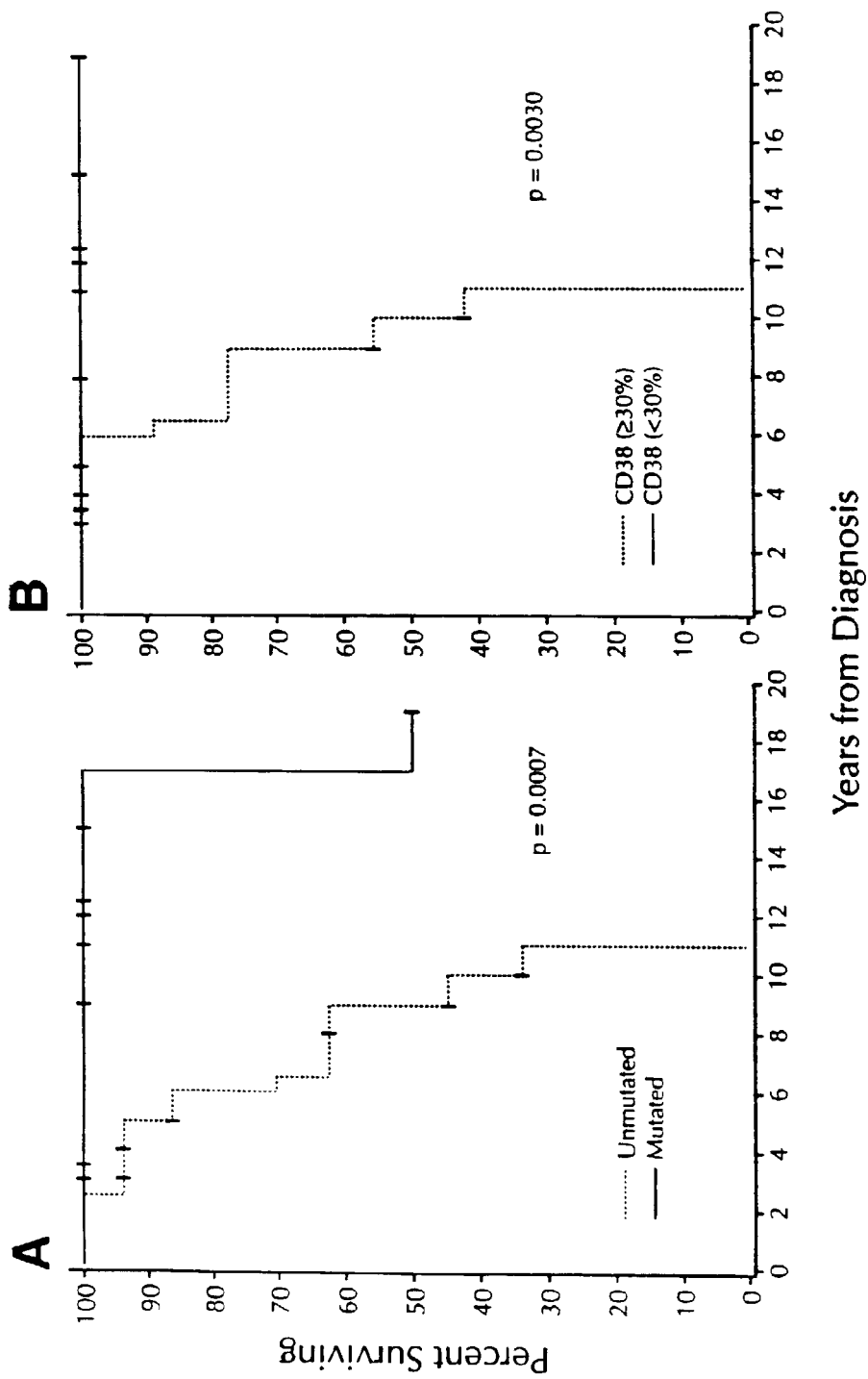
FIG. 4 depicts survival based on V gene mutation status and CD38 expression among B-CLL patients who stratify to the Rai intermediate risk category. Panel A is a Kaplan-Meier plot comparing V gene mutation status with survival among the cases within the Rai intermediate risk category (unmutated: 16 cases; mutated: 9). These cases are frustratingly difficult for clinicians to treat because they can have either an indolent course requiring no or minimal therapy, or a rapid downhill course despite aggressive treatment.

Possibly the most clinically relevant correlation was found among those patients who presented initially in the Rai intermediate risk category (FIG. 4).

These patients are frustratingly difficult for clinicians to treat because they can have either an indolent course requiring no or minimal therapy or a rapid downhill course despite aggressive treatment. Both CD38 expression and V gene mutation status were able to segregate those Rai intermediate risk patients who followed an indolent course from those whose course was much more aggressive (FIG. 4).

Relevant to observations on Ig V gene mutations and survival is the study of Oscier et al (*Blood* 89:4153-60, 1997), indicating that B-CLL cells with unmutated $V_H$ genes frequently contain three copies of chromosome 12, a cytogenetic marker that is associated with poor clinical outcome. This study was recently extended by Hamblin et al (*Blood*, 1999 Sep 15;94(6):1848-54) to a larger cohort of patients. These new data are consistent with the observations herein and show clearly that unmutated $V_H$ genes are associated with a more aggressive form of B-CLL.

When the subject patients were stratified according to V gene mutation status or CD38 expression (Tbl. 3), a clear preponderance of males was noted in the unmutated and ≧30% CD38+ (poor outcome) groups (M:F: 11:1 and 7.5:1, respectively). These ratios are much higher than those reported previously (Catovsky, et al., *Br J Haematol* 72:141-9, 1989). The subject data, however, agree with the studies (Catovsky, et al, supra; Mandelli, et al., supra, *J Clin Oncol* 5:398-406, 1987) indicating that women with B-CLL have a more favorable clinical course than men. Although women comprised only ~10% of the unmutated and ≧30% CD38+ (poor outcome) groups, they constituted ~50% of the mutated and <30% CD38+ (good outcome) groups (Tbl. 3). These data support a role for gender indirectly influencing clinical outcome and possibly B cell maturation and differentiation. The mechanism(s) responsible for these differences are obscure at this point.

The two sets of B-CLL cases characterized in this study appear to represent B cells transformed at different stages of B cell differentiation and/or activation. Thus, those B-CLL cases with mutated V genes and low numbers of CD38+ B-CLL cells are characteristic of post-GC, memory B cells (Clark, *Annu Rev Immunol* 9:97-127, 1991; Pascual, et al, *J Exp Med* 180:329-39, 1994). Some of these B-CLL cells may be derived from the small subset of IgM+/IgD+ memory cells found in the blood (Klein, et al, *J Exp Med* 188:1679-89, 1998) or bone marrow (Paramithiotis and Cooper, *Proc Natl Acad Sci USA* 94:208-212, 1997) or from cells similar to the IgD$^+$ memory B cells identified in tonsils (Arpin, et al., *J Exp Med* 187:1169-78, 1998). Although CD27 is another marker that distinguishes pre-GC from post-GC B cells (Klein, et al, supra, *J Exp Med* 188:1679-89, 1998; Agematsu, et al., *J Immunol* 153:1421-9, 1994; Tangye, et al., *J Exp Med* 188:1691-703, 1998), differences in CD27 expression among the subject CD5$^+$ B-CLL cases were not found, either in density per cell or in cell number (data not shown). These data are in agreement with those of others (Ranheim, et al, *Blood* 85:3556-65, 1995; Trentin, et al., *Cancer Res* 57:4940-7, 1997).

In contrast, those B-CLL cases with unmutated V genes and high numbers of CD38$^+$ B-CLL cells display surface markers characteristic of B cells that have not entered a GC. Since CD38, as detected by mAb conjugated with PE (phycoerythrin), is expressed on most blood B cells (Kumagai, *J Exp Med* 181:1101-10, 1995), the ≧30% CD38$^+$/unmutated B-CLL cells could be derived from either naive B cells or activated B cells that have not entered a GC and have not generated Ig V gene mutations. Based on analyses of the HCDR3 characteristics of unmutated B-CLL cases (Fais, et al, supra, *J Clin Invest* 102:1515-25, 1998; Johnson, et al., *J Immunol* 158:235-46, 1997), a favored hypothesis is that some of these unmutated B-CLL cells have been activated and selected by antigen.

The physiological significance of CD38 expression primarily by the unmutated cases and its potential function in cell survival and proliferation is presently unknown. However, previous studies suggest that CD38 expression identifies those B-CLL clones that are capable of transducing signals through their B cell antigen receptors that may increase or decrease their chance for survival (Lam, et al., *Cell* 90:1073-83, 1997; Zupo, et al., *Eur J Immunol* 24:1218-1222, 1994). In this regard, Zupo et al have reported that CD38$^+$ B-CLL cells can be induced to undergo apoptosis in vitro after exposure to anti-Ig antibodies, whereas CD38$^-$ B-CLL cells are resistant to these effects. These data are at variance with the unexpected subject clinical observations that those B-CLL cases with higher percentages of CD38$^+$ B cells have a worse clinical outcome. However, it is possible that the quality of the antigen receptor stimulus and the presence of associated stimuli may lead to diverse endpoints (apoptosis vs. survival). Similarly, triggering through the CD38 molecule can have different effects on the survival of B cells depending on the state of maturation/activation of the cell. Whereas anti-CD38-mediated signaling results in the death of immature B cells (Kumagai, supra, *J Exp Med* 181:1101-1-, 1995), mature B cells can be rescued from apoptosis by CD38 triggering (Lam, et al., supra, *Cell* 90:1073-83, 1997; Zupo, et al, supra, *Eur J Immunol* 24:1218-1222, 1994). Further studies will be necessary to determine how these in vitro data correlate with the subject clinical observations.

Figure 2:
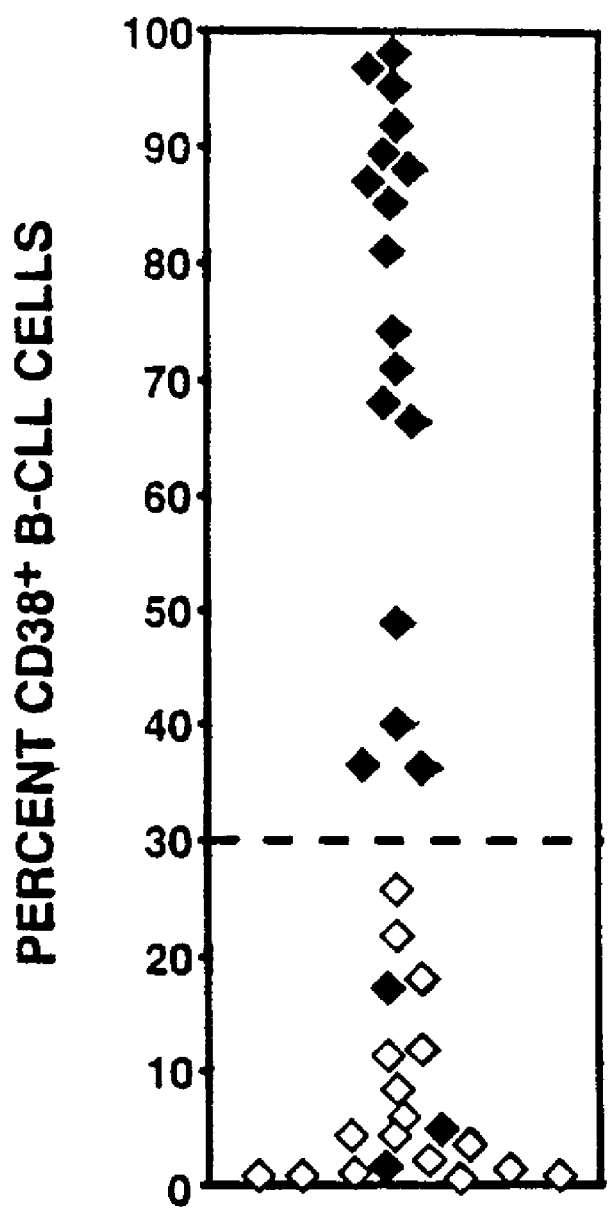
FIG. 2 illustrates the percentages of CD38-expressing B-CLL cells among patients (n=37) whose Ig $V_H$ and $V_L$ genes had been sequenced by the inventor and his colleagues. As established by convention, unmutated cases (♦) were defined as cases displaying <2.0% differences from the most similar germline gene; mutated cases (◊) display $\geq 2\%$ differences. Note that all the cases (17/17) that have $\geq 30\%$ $CD38^+$ B-CLL cells were unmutated, whereas only three unmutated cases expressed low numbers (<30%) of $CD38^+$ B-CLL cells. These comparisons are statistically significant (p=0.00001; Mann-Whitney test).

In conclusion, the present studies identify CD38 expression and V gene mutation status as novel and independent prognostic indicators that appear to identify mutually overlapping groups of B-CLL patients (FIGS. 1 and 2 and Results). However, since CD38 expression can be determined more conveniently and rapidly than Ig V gene mutations, this parameter may be the preferred adjunct to the current staging systems.

Indeed, the results of this simple test should enable physicians to predict with considerable accuracy whether a patient is likely to have a favorable or unfavorable clinical course. Furthermore, since the leukemic cells appear to be fixed in their level of expression of this marker, determining the percentage of CD38$^+$ B-CLL cells may be useful at any point in the clinical course of the individual B-CLL patient. However, the possibility that CD38 expression might change with the alterations in chromosomal structure and gene expression that occur in Richter's transformation cannot be excluded (Koduru, et al., *Br J Haematol* 85:613-616, 1993).

All publications mentioned herein above are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for determining indications of the prognosis of and aggressiveness of disease in a subject with B cell chronic lymphocytic leukemia ("B-CLL"), the method comprising:
   measuring CD38 expression by B-CLL cells in a blood sample from the subject;
   determining the percentage of B-CLL cells in the sample that are CD38$^+$; and
   comparing said percentage to a cut-off value,
   wherein a percentage of CD38$^+$ B-CLL cells from the subject that is greater than or equal to the cut-off value indicates a poor prognosis and an aggressive disease course and a percentage of CD38$^+$ B-CLL cells from the subject that is less than the cut-off value indicates an indolent disease course,
   wherein the cut-off value is determined by:
   measuring CD38 expression by B-CLL cells in a blood sample from each of a cohort of B-CLL patients;
   determining the percentage of B-CLL cells that are CD38$^+$ in each of the cohort patients:
   determining whether the B-CLL in each of the cohort patients is aggressive or indolent; and
   plotting the percentage of B-CLL cells that are CD38$^+$ in the cohort patients vs. aggressiveness or indolence in the cohort patients to establish a cut-off value that distinguishes between patients with aggressive disease and patients with indolent disease.

2. The method of claim 1, wherein B-CLL cells are determined as CD5$^+$ and CD19$^+$.

3. The method of claim 1, wherein CD38 expression of B-CLL cells is determined using flow cytometry.

4. The method of claim 1, wherein the B-CLL patients are IgM$^+$ B-CLL patients.

5. The method of claim 1, wherein measuring CD38 expression by B-CLL cells in a blood sample from each cohort patient is determined prior to measuring CD38expression by B-CLL cells in a blood sample from the subject.

6. A method for evaluating whether a subject with B cell chronic lymphocytic leukemia ("B-CLL") should undergo an aggressive course of treatment, the method comprising
   measuring CD38 expression by B-CLL cells in a blood sample from the subject;
   determining the percentage of B-CLL cells in the sample that are CD38$^+$; and
   comparing said percentage to a cut-off value,
   wherein a percentage of CD38$^+$ B-CLL cells from the subject that is greater than or equal to the cut-off value indicates the subject should undergo an aggressive course of treatment and a percentage of CD38$^+$ B-CLL cells from the subject that is less than the cut-off value indicates the subject should not undergo an aggressive course of treatment,
wherein the cut-off value is determined by:
  measuring CD38 expression by B-CLL cells in a blood sample from each of a cohort of B-CLL patients;
  determining the percentage of B-CLL cells that are CD38$^+$ in each of the cohort patients;
  determining whether the B-CLL in each of the cohort patients is aggressive or indolent; and
  plotting the percentage of B-CLL cells that are CD38$^+$ in the cohort patients vs. aggressiveness or indolence in the cohort patients to establish a cut-off value that distinguishes between patients with aggressive disease and patients with indolent disease.

7. The method of claim 6, wherein B-CLL cells are determined as CD5$^+$ and CD19$^+$.

8. The method of claim 6, wherein CD38 expression of B-CLL cells is determined using flow cytometry.

9. The method of claim 6, wherein the B-CLL patients are IgM$^+$ B-CLL patients.

10. The method of claim 6, wherein measuring CD38 expression by B-CLL cells in a blood sample from each cohort patient is determined prior to measuring CD38 expression by B-CLL cells in a blood sample from the subject.

* * * * *